United States Patent [19]
van Swam et al.

[11] Patent Number: 4,879,088
[45] Date of Patent: Nov. 7, 1989

[54] METHOD AND APPARATUS FOR DETECTING FAILED FUEL RODS (ENC-189)

[75] Inventors: Leo F. van Swam, Richland; Thomas R. Blair, Kennewick; Quang D. Ho, West Richmond, all of Wash.

[73] Assignee: Advanced Nuclear Fuels Corporation, Bellevue, Wash.

[21] Appl. No.: 165,681

[22] Filed: Mar. 8, 1988

Related U.S. Application Data

[63] Continuation-in-part of Ser. No. 65,185, Jun. 17, 1987, abandoned, which is a continuation of Ser. No. 660,786, Oct. 15, 1984, abandoned.

[51] Int. Cl.$^4$ .............................................. G21C 17/06
[52] U.S. Cl. ...................................... 376/252; 73/592; 73/622
[58] Field of Search ......................... 73/592, 616, 622; 376/252

[56] References Cited

U.S. PATENT DOCUMENTS

| 4,174,255 | 11/1979 | Lawrie | 376/252 |
| 4,313,791 | 2/1982 | Lawrie et al. | 376/252 |
| 4,684,493 | 8/1987 | Gravelle | 376/252 |
| 4,689,193 | 8/1987 | van Swam et al. | 376/252 |

Primary Examiner—Deborah L. Kyle
Assistant Examiner—Richard W. Wendtland
Attorney, Agent, or Firm—Volker R. Ulbrich; R. Keith Sharp

[57] ABSTRACT

Nuclear fuel rods are checked for the presence of water in their interior by injecting bursts of ultrasound radially into the wall of each tube, producing echoing back and forth between the inner and outer surfaces of the tube. The rate of decay of this echoing indicates whether or not water is present.

5 Claims, 6 Drawing Sheets

METHOD AND APPARATUS FOR DETECTING FAILED FUEL RODS (ENC-189)

This is a continuation-in-part of application Ser. No. 065,185, filed June 17, 1987, which is a continuation of application Ser. No. 660,786, filed Oct. 15, 1984.

BACKGROUND OF THE INVENTION

By far, the majority of nuclear power reactors are water cooled and moderated reactors, utilizing enriched uranium dioxide as fuel. The core of the reactor is formed by elongated fuel rods which are grouped into bundles which are generally square in cross section. The rods have diameters usually in the range of one-fourth to one half inch and may be ten or twelve feet long. They are held parallel and closely spaced from each other. Each rod is formed of a jacket or "cladding" made of zirconium alloy or stainless steel, which is filled with the uranium dioxide. Most commonly, the uranium dioxide is in the form of pellets which are just enough smaller than the cladding to slide in conveniently. The uranium dioxide may, on the other hand, be in the form of microspheres or granules which are compacted within the cladding. The remainder of the space within the cladding is commonly filled with helium, which has a high thermal conductivity. The helium is frequently under higher than atomspheric pressure.

During the operation of the reactor, holes may develop in the cladding due to stress, corrosion, wear, or defective welding to the end plugs which close the ends of the cladding tubes. If this happens, the helium and fission gases will escape into the cooling water of the reactor and the water will enter the cladding tubes.

After a given fuel assembly has been exposed in the reactor for a given length of time, it is taken out, checked for defects, repaired if necessary, and either returned to the reactor or sent for reprocessing or permanent storage. If the assembly is to be returned to the reactor, it is almost essential that it be checked for defective fuel rods. These irradiated assemblies are highly radioactive and must be stored and inspected under water in order to remove heat caused by the decay of fission products as well as to protect persons working with them. It is therefore highly desirable to provide a method of testing fuel rods for leaks while they are assembled and underwater. One method of doing so is by ultrasonic testing. Such a method is disclosed in U.S. Pat. No. 4,313,791, granted Feb. 2, 1982 and assigned to the Babcock and Wilcox Company. In this method, a transducer emitting ultrasonic vibrations is placed against a fuel rod and an ultrasonic beam is transmitted into the rod by the transducer. The test is performed on a portion of the fuel rod which does not contain uranium dioxide. An analysis of the waves received by a pulse-echo system, reveals whether or not this portion of the rod is filled with water. It is disclosed as carried out at the lower plenum of a fuel rod and apparently would not be operative in a portion of a rod where uranium dioxide is present.

A weakness of this method lies in the fact that many, probably most, fuel rods do not have a lower plenum.

SUMMARY OF THE INVENTION

We have devised an ultrasonic test for failed fuel rods which is an improvement on prior systems. According to out invention, a transducer is traversed through a fuel assembly, spaced from a row of rods which is to be checked. During the traverse, a series of ultrasonic pulses is emitted from the transducer in the form of a beam. When the beam strikes a fuel rod, it is reflected from the outer surface. If the beam is exactly normal to the surface, it will be reflected back into the tansducer to a maximum degree. By the use of well-known electrical systems, this gives rise to an electrical signal. This method is termed the "pulse-echo" technique. Not all of the ultrasonic beam is reflected at the outer surface, however. A portion continues in the tubing wall and strikes the inner surface of the cladding. In a perfect rod, this is in effect a metal-gas interface. No matter how close the fit between the tube and the uranium dioxide, the contact is not sufficient for efficient transfer of sound energy. Neither is the ultrasound transmitted by the helium gas to any substantial degree. There is, therefore, a reflection from the inner surface of the tubing as well as from the outer surface. In fact, the ultrasound is reflected back and forth between the inner and outer walls of the tubing, producing what is termed "wall ringing". This wall ringing is recorded by the electronic system referred to above. If the tube has filled with water, there will be a transfer of the ultrasonic energy from the tubing wall into the water, where it is effectively dispersed. This greatly attenuates the wall ringing. It is immaterial whether uranium dioxide is present or not. The "coupling" of the cladding to the water within the tube results in the attenuation of the wall ringing and so identifies a defective tube.

More specifically, as the transducer is moved along a row of fuel rods, it continuously emits a series of ultrasonic pulses. Typically, the ultrasound has a frequency of 10–30 megahertz and the pulses have a repetition rate of 1–8 kilohertz. When it receives a maximum echo from the outer surface of a fuel rod, a signal is transmitted to a recording medium, e.g., a strip chart. This is done over a pre-selected period of time which may be termed a "time window". After a delay, which is chosen in accordance with the thickness and other characteristics of the cladding, the echo from the "wall ringing" is sampled during another "time window" and, if its amplitude is above a preselected threshold, a second signal is transmitted to the recording medium. Absence of this second signal indicates that water is present within the tube and that the latter is defective.

Our invention also includes apparatus for effectively carrying out the method described above. The transducer is mounted on a probe which is so constructed as to provide the proper spacing between the tubes to be tested and the transducer, and also for the proper positioning of the transducer so that the beam will be perpendicular to the fuel rod axes. We have also provided an indexing system which permits the probe to be accurately and rapidly inserted into the fuel assembly while the latter is under water.

This indexing system includes a plate having grooves which are parallel to the rows of fuel rods which are to be checked and which are spaced apart the same distance as the rows. A reciprocating system acting along those grooves moves the probe along the rows of fuel elements in the assembly. When the reciprocating element is retracted, a pressure medium autuomatically moves it to the next groove, and in this manner, the assembly can be checked very quickly. This indexing system is claimed in an application of Leo F. van Swam and Quang D. Ho, Ser. No. 660,787, filed Oct. 15, 1984 and assigned to the assignee of this application, now U.S. Pat. No. 4,689,193, granted Aug. 25, 1987.

DETAILED DESCRIPTION

Figure 4:
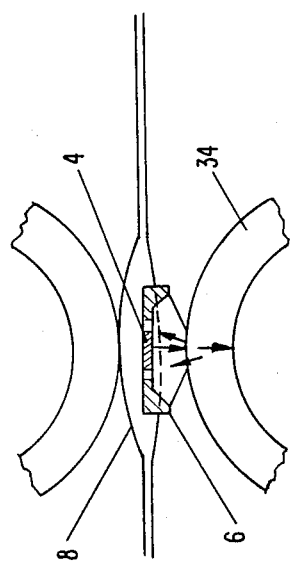
FIG. 4 is a diagrammatic view, partially in section, showing the probe head at the time of making a test.
Figure 1:
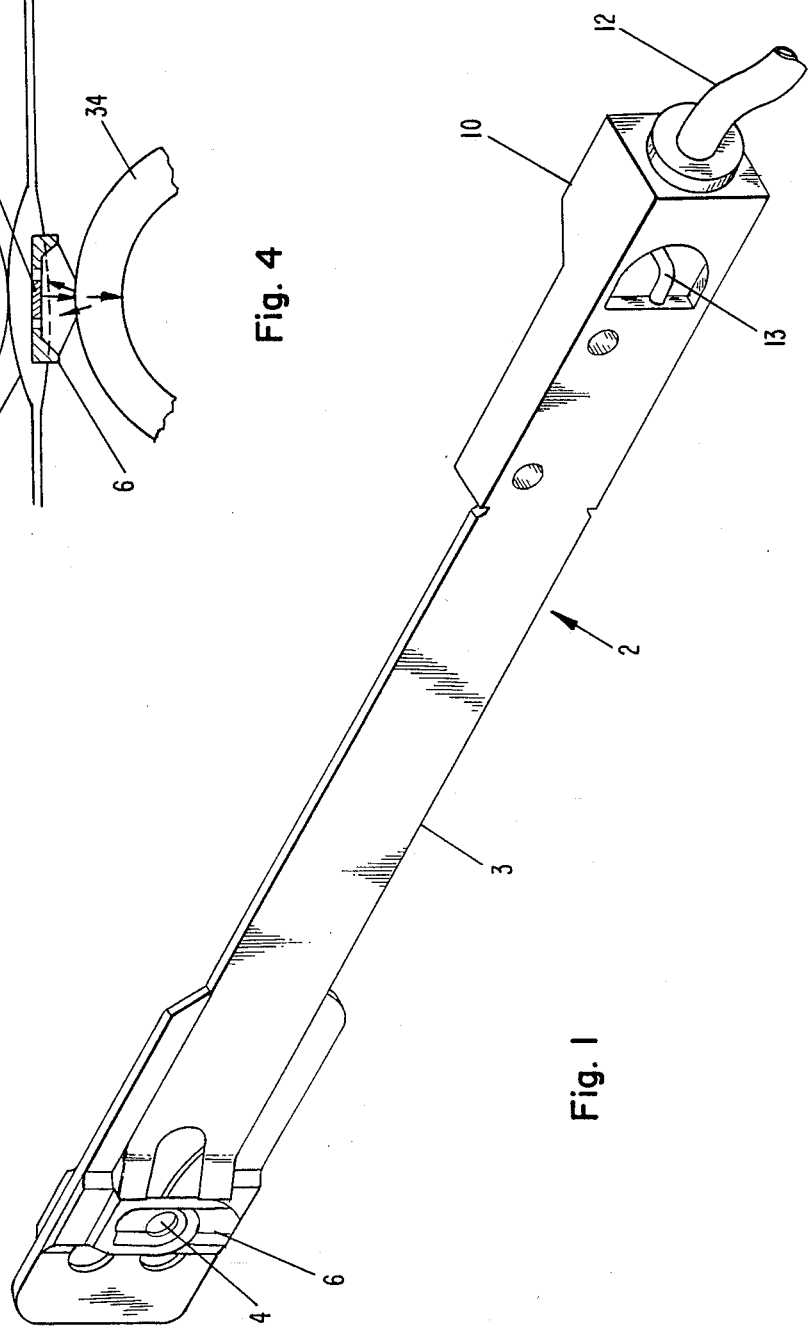
FIG. 1 is a perspective view of a probe forming part of our invention.

Referring to the drawings, FIG. 1 shows the basic probe structure 2 used in our test. It includes a torsionally flexible probe handle 3, near one end of which is a transducer 4. The transducer is mounted in an alignment tab 6, which is spaced from a leaf spring 8 (FIG. 4). At the other end of probe handle 3 is a mounting block 10 which serves as the connector for the electrical cable 12. Probe handle 3 is fabricated from two strips of stainless steel which are welded together. Signal wires 13 connect transducer 4 to cable 12.

Figure 2:
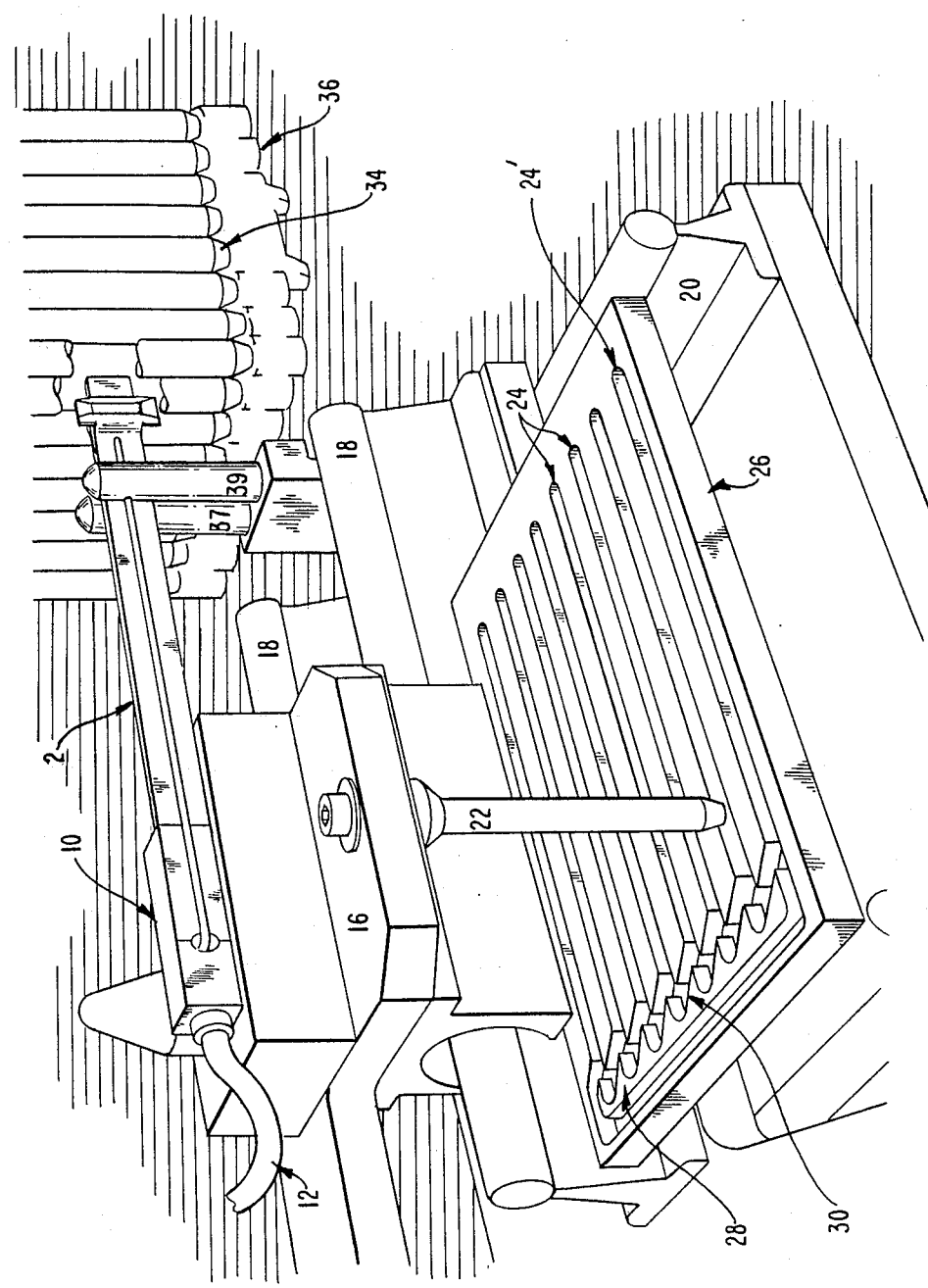
FIG. 2 is a perspective view of our apparatus in relation to a fuel assembly being tested.
Figure 3:
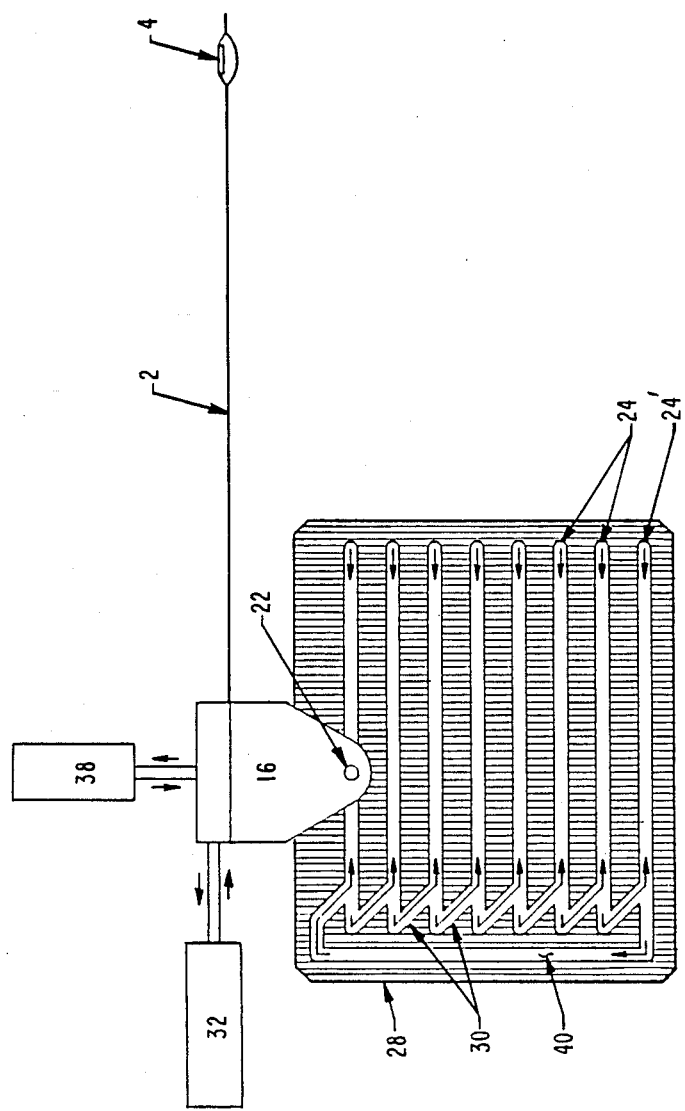
FIG. 3 is a diagrammatic view showing the operation of the apparatus of FIG. 2.
Figure 3A:
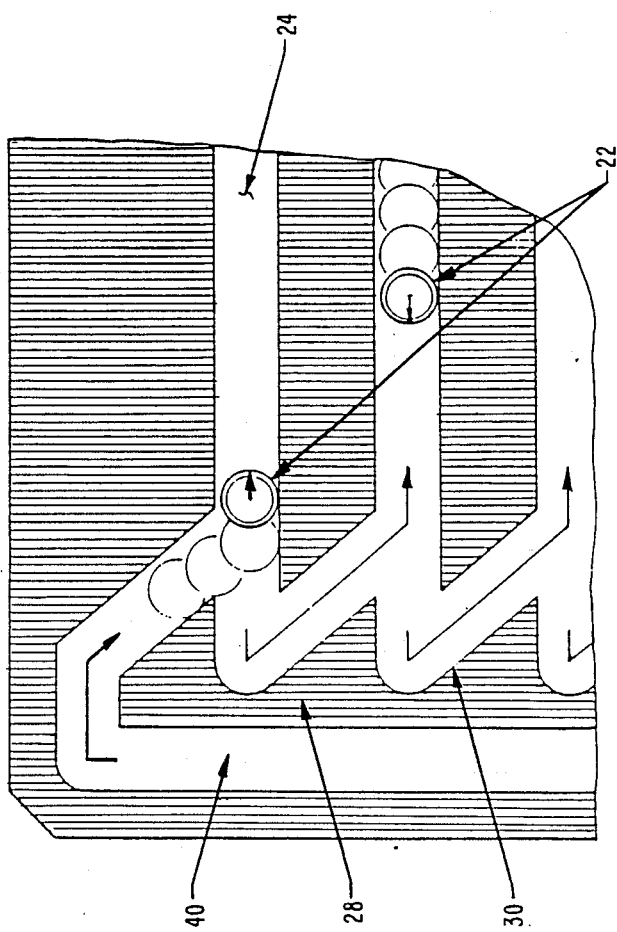
FIG. 3A is an enlarged diagrammatic view of a portion of plate 26 (FIG. 3), showing the movement of pin 22.

FIGS. 2, 3, and 3A show the operating means by which the probe is inserted into the fuel assembly. The mounting block 10 is carried on a support means 16, which rides on rails 18, 18', which provide for longitudinal movement, and on rails 20, which provide for transverse movement. A guide pin 22 slides in grooves 24 of index plate 26. The grooves 24 are open at one end, shown at the left in FIGS. 2 and 3 and are faced by deflection plate 28 which is provided with multiple deflecting surfaces 30, each of which faces one of the grooves 24. The actuating means, which are not shown on FIG. 2, are indicated diagrammatically on FIG. 3. A reciprocating hydraulic cyclinder 32 moves carrier 16 and probe 2 longitudinally of the latter so that the transducer is moved along a row of fuel rods 34 in fuel assembly 36. At the same time, another cylinder 38 exerts a continuous pressure laterally. Under the influence of these cylinders, the pin 22 moves longitudinally along a groove 24 to the right in FIG. 2, then returns. When it reaches the lefthand end of the groove, the force of pressure cylinder 38 forces it laterally along the deflecting surface 30 to the next groove 24, as best shown in FIG. 3A. These grooves are spaced apart the same distance as the spaces between the rows of fuel elements 34. The transducer, therefore, passes successively along the rows of fuel elements in the fuel assembly 36. When the pin 22 has moved in both directions along the last groove 24, indicated as 24', the operator reverses the direction of pressure exerted by cylinder 38. The pin 22 then moves back along the groove 40 at the end of index plate 26 to the starting position, carrying with it the carrier 16 and the probe 2.

Members 37 and 39 are guide members, made in the same form as the fuel tubes 34. One of these members is open at both ends. When the system is immersed in water, it fills, so that it simulates a defective fuel tube. This provides a check on the operation of the system during actual testing.

FIG. 4 shows the position of the transducer 4 relative to a tube 34 when a test is made. As the probe is inserted between the rows of tubes 34, the transducer 4 continuously emits a series of pulses. When the transducer is in most positions of its travel, no reflection from a tube is returned to it. However, when it is in the position shown in FIG. 4, the ultrasound waves follow the paths shown by the arrows, resulting in echoes received and recorded by the transducer. As can be seen in FIGS. 1 and 4 the transducer 4 is recessed within the alignment tab 6 which is pressed against the rod 34 which is being tested. This results in a "water path", indicated by arrows in FIG. 4, between the transducer and the outer surface of the rod 34. This water path is necessary to provide a suitable time interval between the transmission of the pulse and the reception of the echoes which will now be described.

Figure 5:
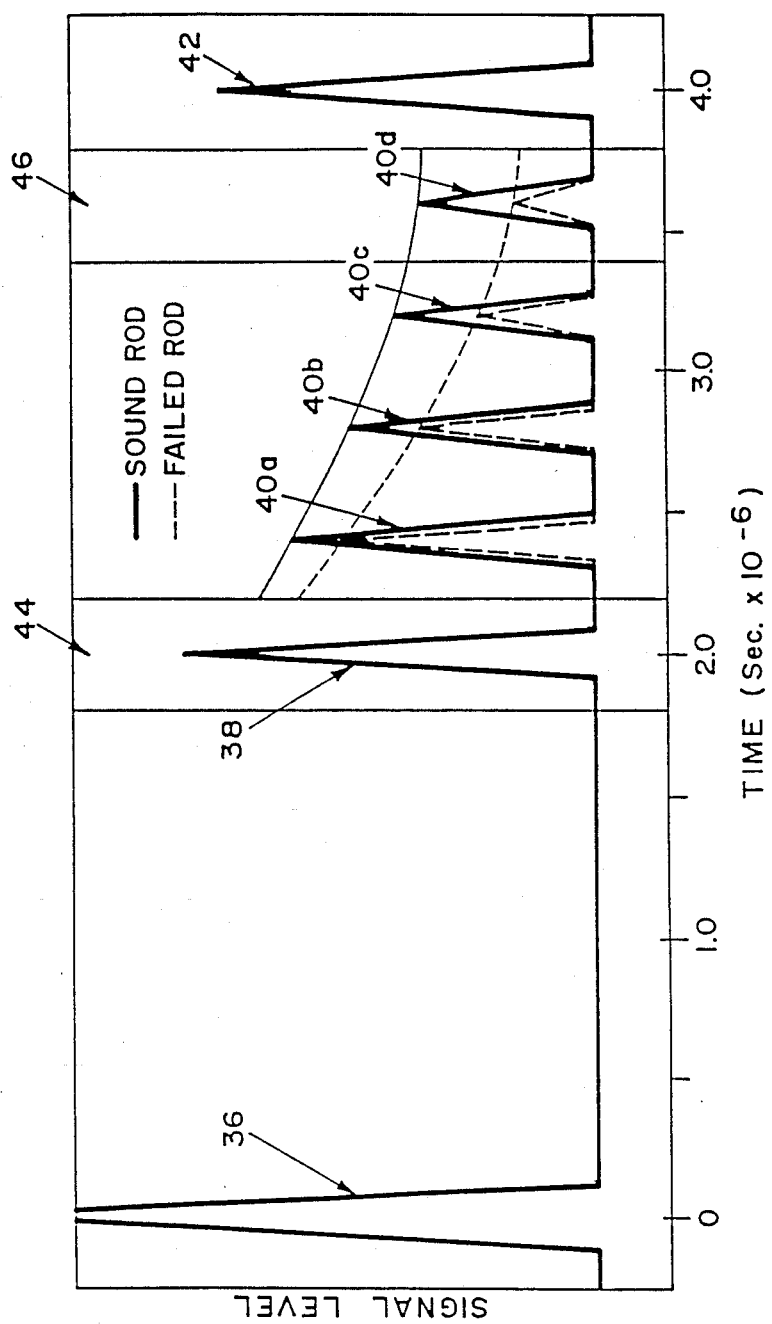
FIG. 5 is a graph based on reproductions of oscilloscope recordings of echoes from a sound and defective fuel rod, respectively.

FIG. 5 shows typical examples of the form of the echo as recorded on an oscilloscope. The horizontal axis of the graph measures time while the vertical axis measures the amplitude of the echoes received by the transducer. FIG. 5 shows, in solid lines, the signals characteristic of a tube which contains no water, and, in dotted lines, those characteristic of a tube containing water. The transducer, as it travels past the rods, emits a series of pulses, one of which is shown at 36. The remaining peaks show various reflections which are received by the transducer when it is aligned so that the emitted beam is radial to the tube. The first peak, 38, is the reflection from the outer surface of the rod. It will be noted that this is received by the transducer about 2.0 microseconds after the transmitted pulse. During the next 1.7 (approximately) microseconds there is a series of closely spaced peaks 40a, 40b, 40c, and 40d. They are from the inner surface of the tube nearest the transducer and are the result of reflection of the ultrasound back and forth between the inner and the outer surface of the tube wall nearest to the transducer. This is termed "wall ringing".

Finally, there is another pulse 42 which results from the reflection of the ultrasound from the outer wall, back to the transducer, again to the outer wall, and again to the transducer. This is termed the "second surface echo".

The curves connecting the peaks show the decay of the "wall ringing" with time. It will be noted that the rate of decay is much greater for a tube containing water than for one free from water. This is because there is a relatively high degree of "coupling", i.e., transfer of energy, between the metal and water, and almost no coupling between the metal and a gas, such as helium. The effect is the same whether of not the portion of the tube being tested contains fuel. The reflected sound energy is a function of boundary condition on the inside of the cladding. As long as the water layer is thick relative to the wave length of the sound being used then material beyond this water layer will have no affect on the measurement. The amount reflected from the fuel, if present, will be small as compared to that reflected from the inner wall of the tube, perhaps 2 percent of it.

Figure 6:
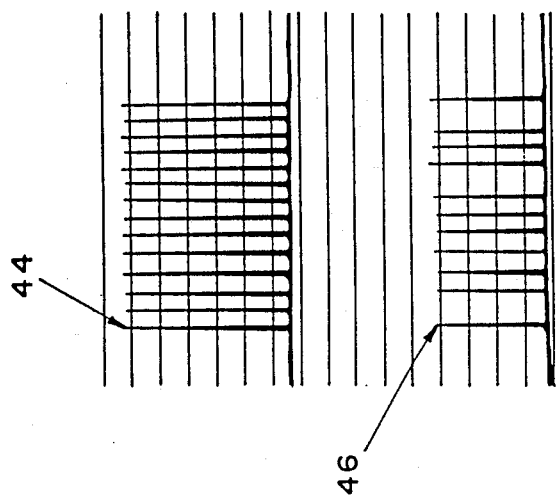
FIG. 6 is a reproduction of strip chart records as the probe is passed along a row of rods.
Figure 7A:
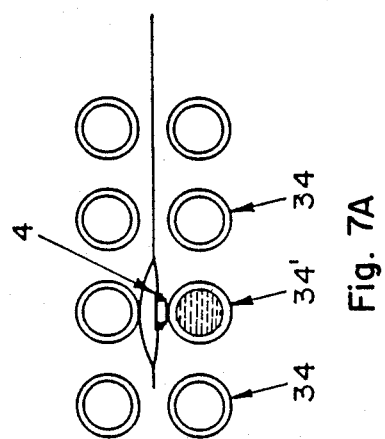
FIG. 7 is a portion of a record like that of FIG. 6 on an expanded time scale and showing the relationship with a row of fuel rods.
Figure 7B:
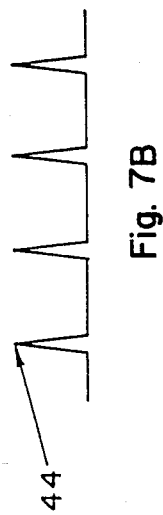
Figure 7C:
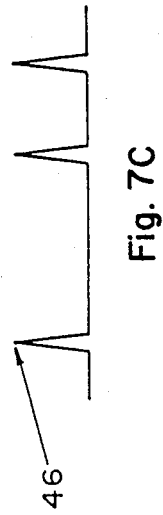

In making the test, the instrumentation is so designed that when the transducer is centered on a rod, there is a recordation over a "time window" 44, which includes the peak 38. After a specified lapse of time, chosen to exclude the second surface echo 42, there is again a recording of the signal over the "time window" 46, which includes the fourth reflection from the inner surface, provided the signal at this time is above a predetermined amplitude. If the signal is below that level, no recording is made. A sample of such a record is shown in FIG. 6. In this figure, the upper row records the echo received in the time windows 44 from each rod traversed by the transducer, while the lower row indicates the signals received during the time windows 46. It will be noted that in some instances there is no recording 46 corresponding to a record 44. The relationship is shown in larger scale and in relation to the tubes in FIG. 7. This figure shows a row of tubes 34 including one defective tube 34' which contains water. The upper signal trace shows the echoes received during the time windows 44. The lower shows echoes received during the time windows 46. It will be noted that no signal 46 appears opposite the defective tube 34'.

The entire traverse of the transducer along a row of tubes 34 (FIG. 2) requires only a very few seconds; hence, an assembly can be checked very quickly with this system.

While we have described in detail one embodiment of our invention, it will be apparent to those skilled in the art that various changes can be made, we therefore wish our patent coverage to be limited solely by the scope of the appended claims.

We claim as our invention:

1. A method of distinguishing nuclear fuel rods containing water from rods free from water, such rods being arranged in an assembly in straight spaced rows, comprising moving a single ultrasonic transducer parallel to one of said rows, but spaced from the fuel rods in said row, and emitting bursts of ultrasound in the direction of said rods and at right angles to their axes; upon reception of an initial echo from a rod, recording said echo on a recording medium and, after a predetermined length of time and for a limited period of time, corresponding to echoing entirely within the cladding wall, recording reception of a second repetitive echo greater than a predetermined threshold, said second echo resulting from echoing back and forth between the outer surface and the inner surface of the cladding of said rod nearest to the transducer, the absence of said second echo above said threshold indicating the presence of water.

2. A method of distinguishing nuclear fuel rods containing water from rods free from water, said rods being arranged in an assembly of straight spaced rows, each of said rods comprising an outer cylindrical metallic cladding and ceramic nuclear fuel in said cladding, comprising:

moving a single ultrasonic transducer parallel to one of said rows but spaced from fuel rods in said row, said transducer being positioned adjacent to a portion of said rods which contain said ceramic fuel and emitting bursts of ultrasound in the direction of said rods and at right angles to their axes;

when said transducer is aligned with the axis of a rod, recording a first echo from the outer surface of the wall of the cladding of said rod nearest said transducer and;

after a predetermined length of time corresponding to echoing back and forth between the outer surface and the inner surface of said cladding wall, recording for a limited period of time the reception of a second repetitive echo greater than a predetermined threshold, said second echo resulting from echoing back and forth between the outer surface and the inner surface of the portion of the cladding wall nearest to the transducer.

3. A method as defined in claim 1, wherein the predetermined length of time between said intitial echo and said second echo is about two microseconds.

4. Apparatus for detecting the presence of water in tubular members, said tubular members being aligned in parallel rows in an assembly, comprising an elongated probe bearing an elongated torsionally flexible handle, at least one tab mounted on said handle near an end, an ultrasonic transmit-receive transducer near said end, said tab extending at right angles to said handle, one face of said tab being adapted to bear against at least one tubular member in a first one of said rows, a spring near the same end and spaced from said tab so as to engage at least one of said tubular members in a second one of said rows adjacent to said first row, said handle, tab, spring and transducer being so related that when said probe is inserted between two rows of tubular members, said transducer will emit a beam at right angles to the axes of said tubular members and receive reflections of said beam.

5. Apparatus as defined in claim 4, wherein said transducer is recessed within the face of the tab which bears against said tubular member.

* * * * *